United States Patent [19]
Evans et al.

[11] Patent Number: 5,670,509
[45] Date of Patent: Sep. 23, 1997

[54] TOCOLYTIC OXYTOCIN RECEPTOR ANTAGONISTS

[75] Inventors: Ben E. Evans; Douglas W. Hobbs, both of Lansdale; Joseph M. Pawluczyk, Plymouth Meeting; Douglas J. Pettibone, Chalfont; Kenneth E. Rittle, Green Lane; Peter D. Williams, Harleysville, all of Pa.

[73] Assignee: Merck & Co., Inc., Rahway, N.J.

[21] Appl. No.: 411,619

[22] PCT Filed: Sep. 27, 1993

[86] PCT No.: PCT/US93/09152

§ 371 Date: Apr. 5, 1995

§ 102(e) Date: Apr. 5, 1995

[87] PCT Pub. No.: WO94/07496

PCT Pub. Date: Apr. 14, 1994

[51] Int. Cl.⁶ ............................ A61K 31/44; C07D 471/10
[52] U.S. Cl. .................................................. 514/278; 546/17
[58] Field of Search ................................ 514/278; 546/17

[56] References Cited

U.S. PATENT DOCUMENTS

| | | | |
|---|---|---|---|
| 3,125,580 | 3/1964 | Jannssen et al. | 260/293 |
| 3,301,857 | 1/1967 | Berger et al. | 260/278 |
| 3,654,287 | 4/1972 | Dykstra et al. | 260/293.62 |
| 3,666,764 | 5/1972 | Campbell et al. | 260/293.62 |
| 4,087,425 | 5/1978 | Garcia et al. | 544/383 |
| 4,379,933 | 4/1983 | Ong et al. | 546/17 |
| 5,091,387 | 2/1992 | Evans et al. | 514/278 |
| 5,204,349 | 4/1993 | Bock et al. | 514/253 |
| 5,206,240 | 4/1993 | Baldwin et al. | 514/231.5 |
| 5,219,860 | 6/1993 | Chambers et al. | 514/278 |

FOREIGN PATENT DOCUMENTS

| | | |
|---|---|---|
| 0 450 761 A1 | 3/1990 | European Pat. Off. . |
| 414289 | 9/1991 | European Pat. Off. . |
| 0 444 945 | 9/1991 | European Pat. Off. . |
| 445974 | 9/1991 | European Pat. Off. . |
| 0 486 280 A2 | 5/1992 | European Pat. Off. . |

OTHER PUBLICATIONS

Chambers et al., Spiropiperidines as High–Affinity, Selective Ligands, J. Med. Chem., 35, 2033–2039 1992.
Evans et al., Orally Active, Nonpeptide Oxytocin Antagonists, J. Med. Chem., 35, 3919–3927 1992.
J. Org. Chem., vol. 36, No. 5, pp. 650–654 (1971), by Matier, et al., entitled Novel. Cyclizations and Ring–Opening Reactions of 3–Phenylindene Derivatives.

*Primary Examiner*—Joseph McKane
*Assistant Examiner*—Richard S. Myers, Jr.
*Attorney, Agent, or Firm*—Mary A. Appollina; Melvin Winokur

[57] ABSTRACT

Compounds of the formula X-Y-Z-R$^1$ wherein:

X is

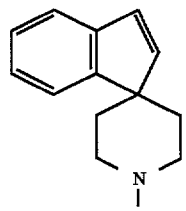

Y is —CO— or —SO$_2$—;

Z is an optional substituent selected from —NH—, —O—, —CHR—, —CH=CH—, —CH=, —(CH$_2$)$_m$— or —CHCHOH—; and R$^1$ is —CH$_3$—, —CH(CH$_3$)$_2$, or substituted phenyl are tocolytic oxytocin antagonists useful in the treatment of pre-term labor, stripping labor preparatory to Caesarean delivery and dysmenorrhea.

11 Claims, No Drawings

TOCOLYTIC OXYTOCIN RECEPTOR ANTAGONISTS

This is a 371 application of PCT application U.S.93/09152 filed Sep. 27, 1993, based on U.S. application Ser. No. 07/957,938, filed Oct. 7, 1992. (now abandoned).

FIELD OF THE INVENTION

The present invention provides novel compounds, novel compositions, methods of their use and methods of their manufacture, such compounds generally pharmacologically useful as agents in obstetric and gynecologic therapy. The aforementioned pharmacologic activities are useful in the treatment of mammals. More specifically, the compounds of the present invention can be used in the treatment of preterm labor, stopping labor preparatory to Caesarean delivery, and in the treatment of dysmenorrhea. At the present time, there is a need in the area of obstetric and gynecologic therapy for such agents.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that a selective oxytocin antagonist would be the ideal tocolytic agent. In the last few years, evidence has accumulated to strongly suggest that the hormone oxytocin may be a physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. A selective oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds of the present invention can also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist can be more efficacious for treating dysmenorrhea then current regimens. An additional use for the present invention is for the stoppage of labor preparatory to Caesarean delivery.

It is, therefore, a purpose of this invention to provide substances which more effectively antagonize the function of oxytocin in disease states in animals, preferably mammals, especially in humans. It is another purpose of this invention to prepare novel compounds which more selectively inhibit oxytocin. It is still another purpose of this invention to provide a method of antagonizing the functions of oxytocin in disease states in mammals. It is also a purpose of this invention to develop a method of preventing or treating oxytocin-related disorders of preterm labor and dysmenorrhea by antagonizing oxytocin.

It has now been found that compounds of the present invention are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. These compounds are useful in the treatment and prevention of oxytocin-related disorders of animals, preferably mammals and especially humans. These disorders are primarily preterm labor and dysmenorrhea. The compounds would also find usefulness for stoppage of labor preparatory to Caesarean delivery.

SUMMARY OF THE INVENTION

The compounds and their pharmaceutically acceptable salts and esters of the present invention are those of the general structural formula:

X-Y-Z-R¹, wherein

X is

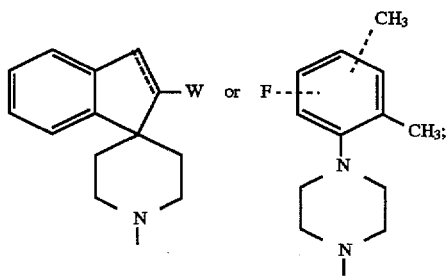

W is hydrogen or acetate;

Y is —CO—, —SO$_2$— —CO(CH$_2$)$_m$— or —(CH$_2$)$_m$—;

Z is an optional substituent that, when present, is one or more of N, O, S, —CHR—, —CR=CH—, —CH=, —(CH$_2$)$_m$— or —CHCHOH—;

R is hydrogen, C$_{1-5}$ alkyl or C$_{1-5}$ alkoxycarbonylamino, quinuclidinylaminocarbonylamino;

$R^1$ is —CH$_3$, —CH(CH$_3$)$_2$, C$_{1-5}$ alkoxycarbonyl,

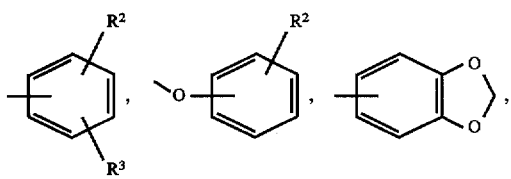

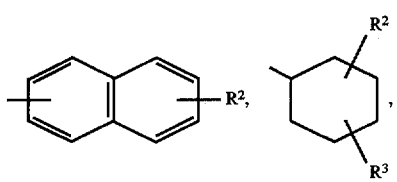

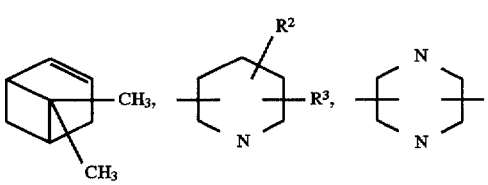

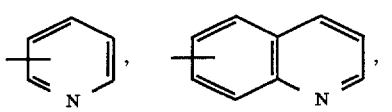

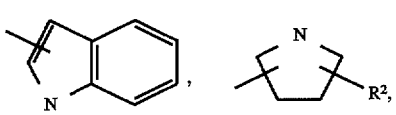

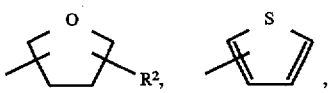

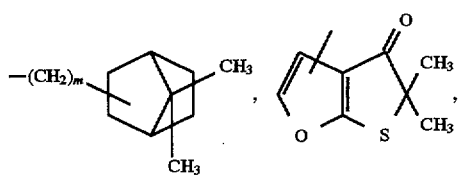

—NR$^4$R$^5$ or —NCOR$^6$;

$R^2$ is hydrogen, hydroxy, carboxyl, acetyl, nitro, cis or trand oximino, halogen, mono, di- or tri-C$_{1-3}$ alkyl, spirocyclic indenyl, N-spiroindanepiperidinyl, O-R where R is as defined above, O-Het where Het is imidazole or benzimidazole or azimidobenzene, or where R$^2$ is further defined as —COR$^6$, —(CH$_2$)$_m$—NHCOR$^7$, —(CH$_2$)$_m$NHCOOR$^7$, —(CH$_2$)$_m$—NR$^8$R$^9$, —(CH$_2$)$_m$—NHCO—(CH$_2$)$_m$R$^7$, —(CH$_2$)$_m$—NHCO—CHR$^7$R$^7$, —(CH$_2$)$_m$—NHCO—CH=CHR$^7$, —(CH$_2$)$_m$—CO—O—R$^7$, —(CH$_2$)$_m$—CO—O— (CH$_2$)$_m$R$^7$, —(CH$_2$)$_m$—CO—O—CHR$^7$R$^7$, —(CH)$_m$—CO—O—CH=CHR$^7$, —NHSO$_2$R—where R is as defined above, NHSO$_2$R$^7$, —(CH$_2$)$_m$—O—R$^{10}$, —SO$_2$R$^{10}$, —COR$^{11}$,

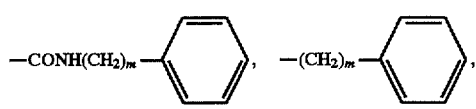

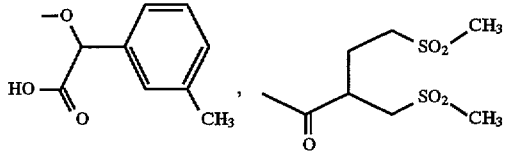

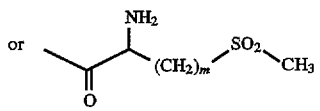

or one to two substituents selected from the group consisting of

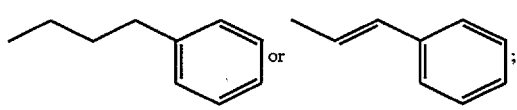

$R^3$ is one or two of hydrogen, hydroxyl or C$_{1-5}$ alkyl;

with the proviso that when R$^1$ is cyclohexyl, then R$^2$ and R$^3$ are limited to being hydroxyl or C$_{1-5}$ alkyl;

$R^4$ is hydrogen, C$_{1-5}$ alkyl, or C$_{6-10}$ cycloalkyl;

$R^5$ is hydrogen or acetyl;

$R^6$ is

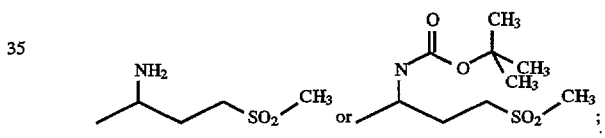

$R^7$ is

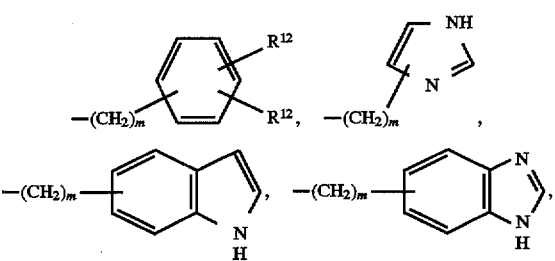

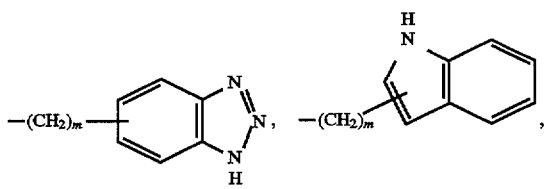

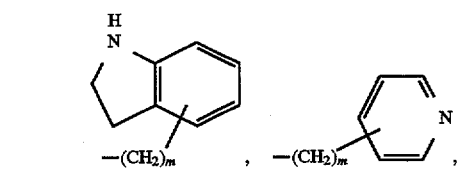

-continued

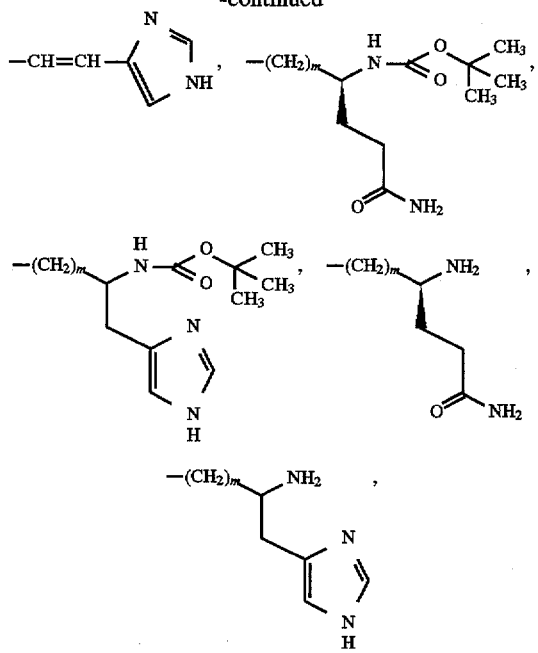

hydrogen, $C_{1-4}$ alkyl, $NSO_2R^{12}$ or $NHO-C_{1-4}$ alkyl;

$R^8$ is hydrogen or $C_{1-5}$ alkyl;

$R^9$ is hydrogen or $C_{1-5}$ alkyl;

$R^{10}$ is $-CH_3$,

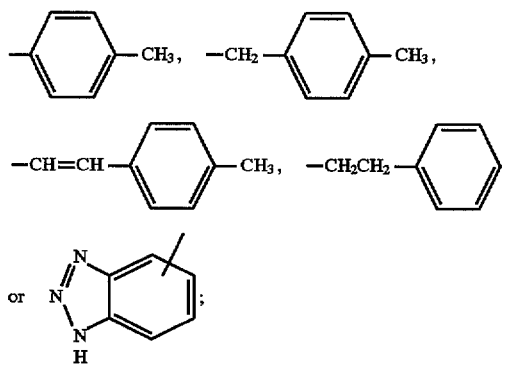

$R^{11}$ is $-CH_3$,

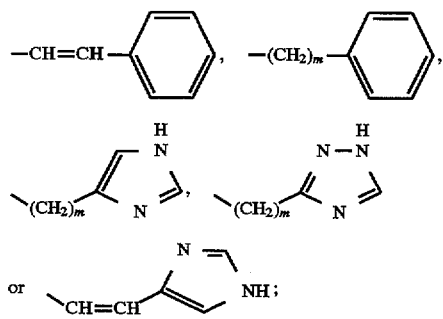

$R^{12}$ is hydrogen, $C_{1-5}$ alkyl or $C_{1-5}$ alkoxy; and m is an integer of from 0 to 5;

with the proviso that when X is

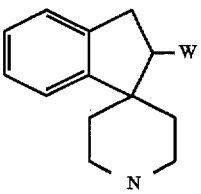

and when $R^1$ is disubstituted phenyl when the phenyl substituents are any of hydroxyl, carboxyl, nitro, halogen, mono-, di- or tri-$C_{1-3}$ alkyl, $C_{1-5}$ alkoxy; or when $R^1$ is pyridyl; or when $R^1$ is $-CH_3$ or $-CH(CH_3)_2$; or when $R^1$ is unsubstituted bicyclo loweralkyl of 9 carbons or unsubstituted or substituted cyclohexyl and the substituent is hydroxyl; then Y is $-(CH_2)_m-$ where m has a value of from 1 to 5.

Salts and esters encompassed within the term "pharmaceutically acceptable salts and esters" refer to non-toxic salts of the compounds of this invention which are generally prepared by reacting the free base with a suitable organic or inorganic acid. Representative salts include the following salts:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulanate | N-methylglucamine |
| Citrate | ammonium salt |
| Dihydrochloride | Oleate |
| Edetate | Oxalate |
| Edisylate | Pamoate (Embonate) |
| Estolate | Palmitate |
| Esylate | Pantothenate |
| Fumarate | Phosphate/diphosphate |
| Gluceptate | Polygalacturonate |
| Gluconate | Salicylate |
| Glutamate | Stearate |
| Glycollylarsanilate | Sulfate |
| Hexylresorcinate | Subacetate |
| Hydrabamine | Succinate |
| Hydrobromide | Tannate |
| Hydrochloride | Tartrate |
| Hydroxynaphthoate | Teoclate |
| Iodide | Tosylate |
| Isothionate | Triethiodide |
| Lactate | Valerate |

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any number within this range.

The term "alkenyl" shall mean straight or branched chain alkenes with one or more degrees of unsaturation at any position on the chain, of two to ten total carbon atoms, or any number within this range.

The term "alkynyl" shall mean straight or branched chain alkynes with one or more degrees of unsaturation at any position on the chain, of two to ten total carbon atoms, or any number within this range.

The term "aryl" shall mean phenyl, naphthyl or fluorenyl.

The term "cycloalkyl" shall mean cyclic rings of alkanes of three to eight total carbon atoms.

Whenever the terms "alkyl" or "aryl" or either of their prefix roots appear in a name of a substituent (e.g. aralkoxyaryloxy) they shall be interpreted as including those limitations given above for "alkyl" and "aryl". Designated numbers of carbon atoms (e.g. $C_{1-10}$) shall refer independently to the number of carbon atoms in an alkyl or cyclic alkyl moiety or to the alkyl portion of a larger substituent in which alkyl appears as its prefix root.

The term "oxo" shall refer to the substituent =O.

The term "azimidobenzene" (also known as benzotriazole) shall refer to the moiety

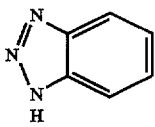

The term "spirocyclic indenyl" shall refer to the moiety

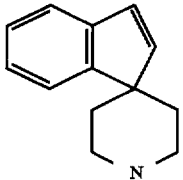

The term "halogen" shall include iodine, bromine, chlorine and fluorine.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "Caesarean delivery" shall mean incision through the abdominal and uterine walls for delivery of a fetus.

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singly or plurally.

The ability of the compounds of formula I to antagonize oxytocin makes these compounds useful as pharmacologic agents for mammals, especially for humans, for the treatment and prevention of disorders wherein oxytocin may be involved. Examples of such disorders include preterm labor and especially dysmenorrhea. These compounds may also find usefulness for stoppage of labor preparatory to Cesarean delivery.

Because of the known relationship of vasopressin to oxytocin, the compounds of the present invention are also useful as vasopressin antagonists. Vasopressin antagonists are useful in the treatment or prevention of disease states involving vasopressin disorders, including their use as diuretics and their use in congestive heart failure.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.3–6.0 gm/day orally. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl- methacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The compounds of formula I can be prepared readily according to the following reaction Schemes (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

SCHEME 1

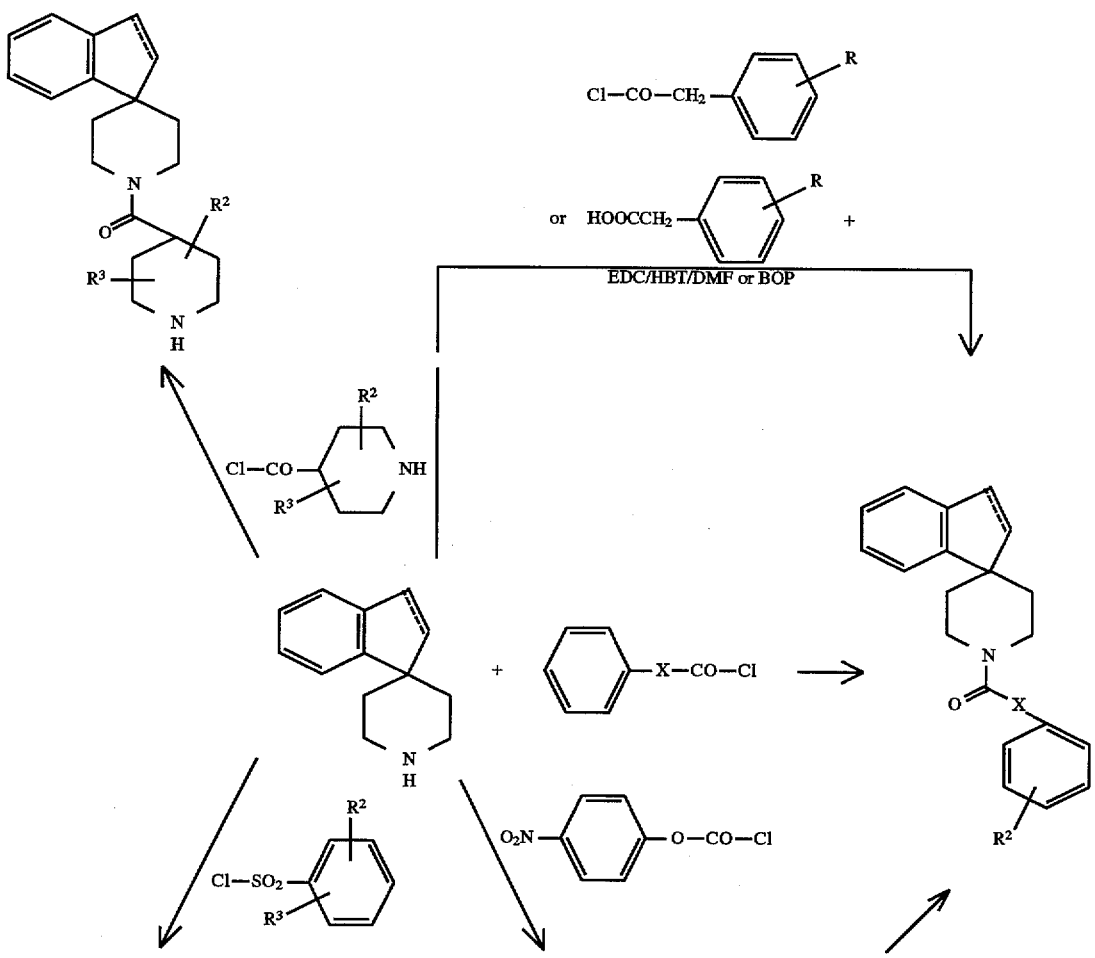

11
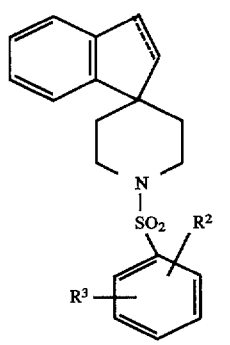
X = O, N, S, CH₂
n = 1,2
-continued
SCHEME 1
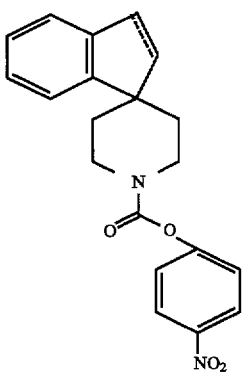
20
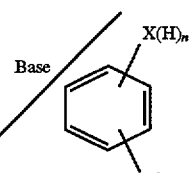
(Where X = N, O or S)
SCHEME 2
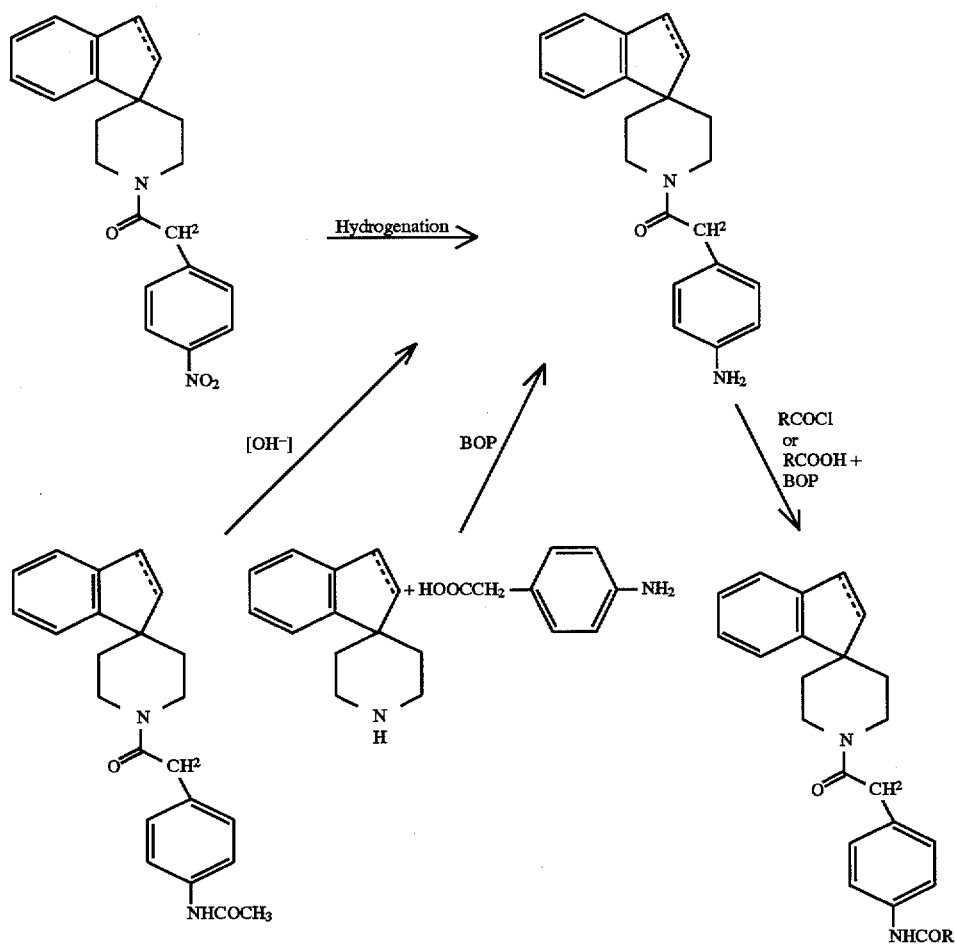

SCHEME 3
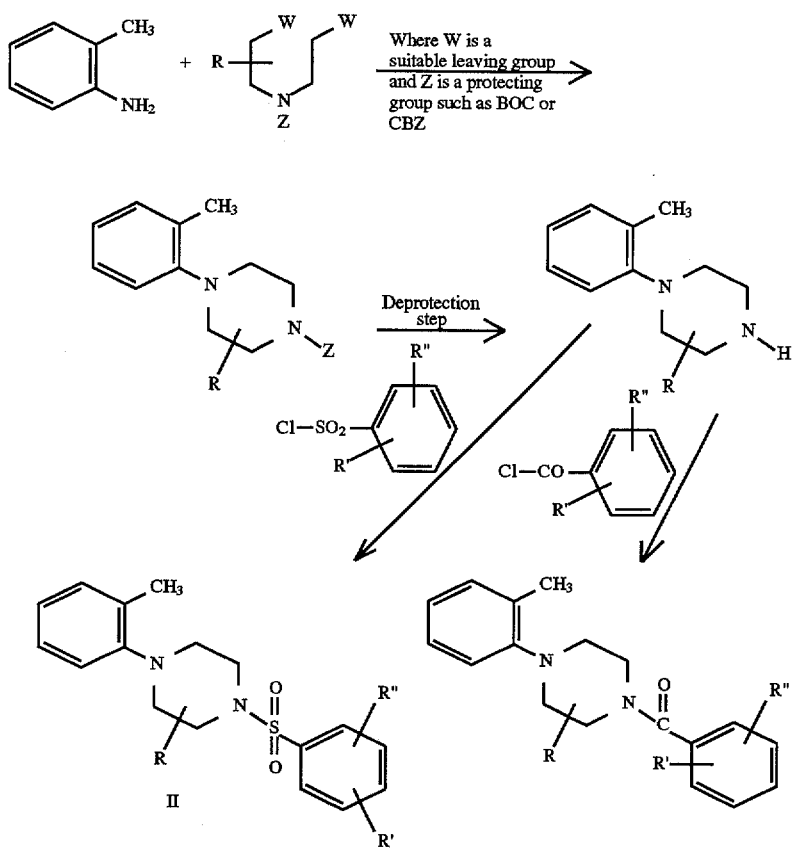
SCHEME 4
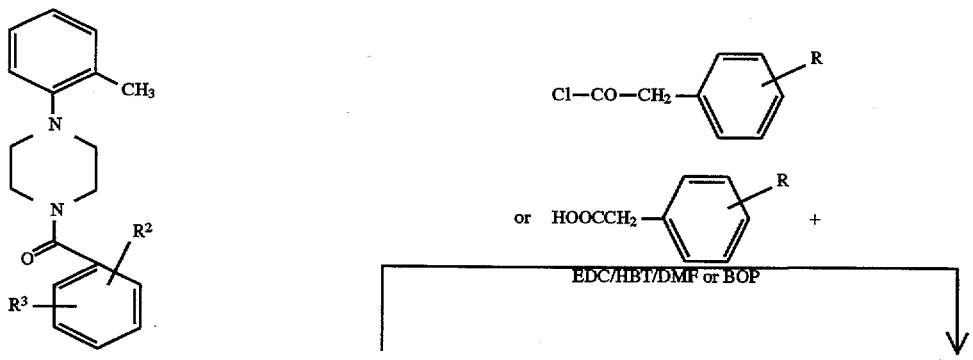

-continued
SCHEME 4

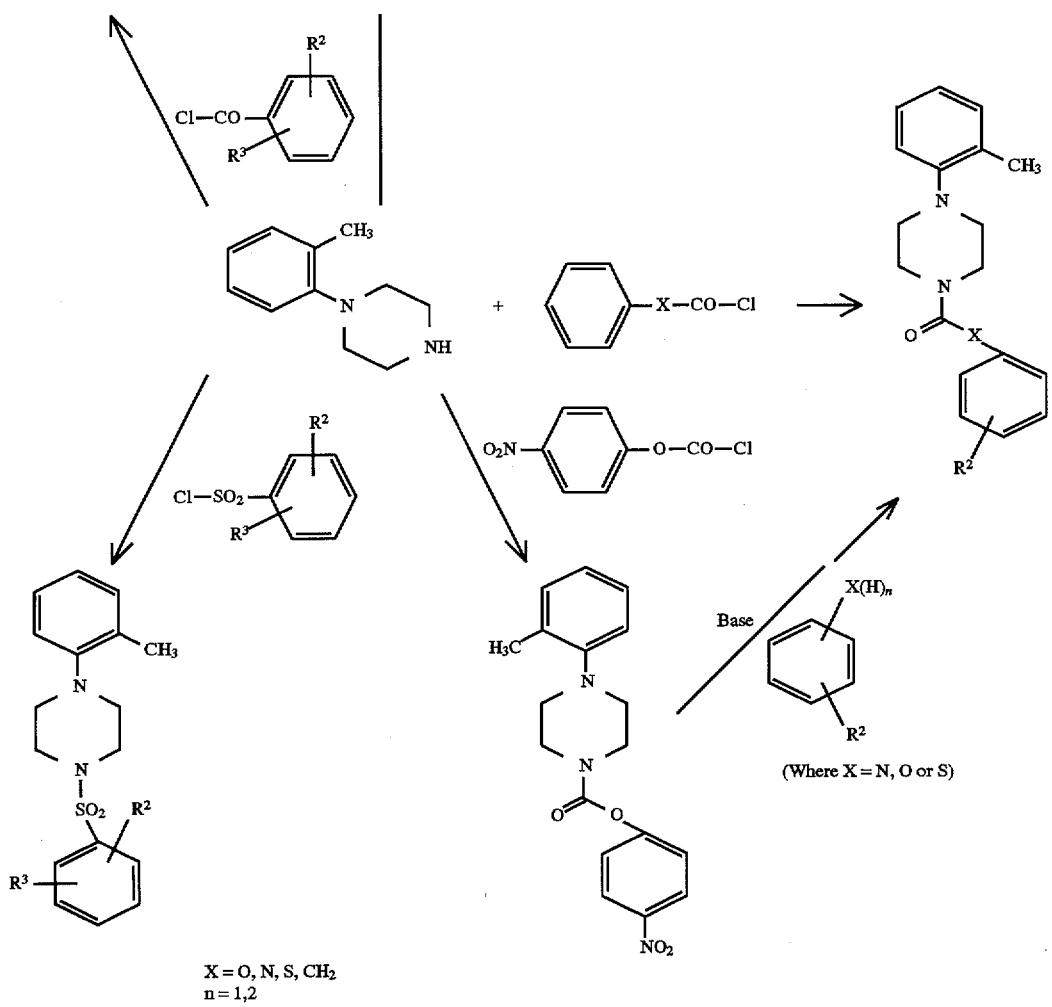

X = O, N, S, CH₂
n = 1,2

Abbreviations used in the Examples are as follows:

EDC=1-ethyl-3-(3-dimethylaminopropyl)carbodiimide hydrochloride
BOC=tert-butoxycarbonyl
TEA=triethylamine
DIEA=diisopropylethylamine
BOP=benzotdazolyloxytris(dimethylamino) phosphonium hexafluorophosphate
THF=tetrahydrofuran
DMF=dimethylformamide
LAH=lithium aluminum hydride
TFA=trifluoroacetic acid
HPLC Method A=15 min. linear gradient 95:5 A:B to 0:100 A:B A—H₂O containing 0.1% by vol. TFA B=CH₃CN containing 0.1% by vol. TFA 2.0 mL/min flow rate 12 cm C₁₈ reverse phase column UV detection (215 nm)
TLC was performed on 20 cm plates coated with silica gel (250 microns) from Analtech.

EXAMPLE 1

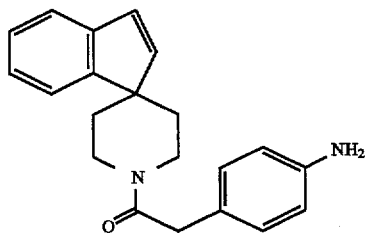

70 mg (0.316 mmol) of spiro(1H-indene-1,4'-piperidine HCl) was dissolved in 3 ml DMF and the solution treated with 52.5 mg (0.347 mmol) of 4-aminophenyl acetic acid followed by 161 mg (0.363 mmol) of benzotriazol-1-yl-oxy (dimethylamino)phosphonium hexafluorophosphate (BOP Reagent). The pH of the solution was adjusted to 9.5 with 142 µl (0.794 mmol) of diisopropylethylamine and the mixture stirred at 25° for 1 hour.

DMF was removed in vacuo and the crude residue treated with water and extracted with ethyl acetate (3×). The organic extracts were combined, washed with water (1×), brine (1×), dried over $Na_2SO_4$, filtered and stripped to dryness in vacuo. Flash chromatography of the crude product on silica gel (1:1 of ethyl acetate: $CH_2Cl_2$) gave the title compound as a white foam (41 mg, 40.6% yield) upon coevaporation with ether (3×) in vacuo.

M.W.: 318.402. m.p.; 60°–87° C. (sinter) HPLC: 96.3% PMR: Consistent with structure plus ether and water M.S.: M+H=319 (FAB). TLC: $R_f$=0.34, Silica GF (1:1 of EtOAc: $CH_2Cl_2$). CHN: Calc'd as $C_{21}H_{22}N_2O \cdot 0.05\ C_4H_{10}O \cdot 0.30\ H_2O$ (F.W.=327.532): C, 77.74; H, 7.11; N, 8.55. Found: C, 77.83; H, 6.80; N, 8.23.

EXAMPLE 2

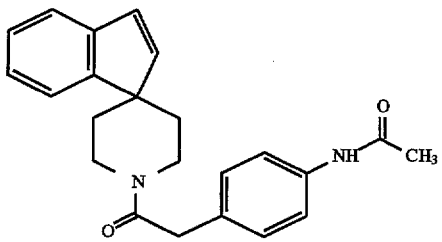

1.1 gm (3.45 mmol) of the product of Example 1 was dissolved in 15 ml of $CH_2Cl_2$ and the solution treated with 0.27 ml (3.80 mmol) of acetyl chloride. The pH was adjusted to 9.5 with 0.55 ml (3.82 mmol) of triethylamine and the mixture stirred at 25° C. for 1 hour.

Flash chromatography of the reaction mixture directly on silica gel (3:1 of ethyl acetate: $CH_2Cl_2$) gave the title compound as a crystalline solid (992 mg, 79.3% yield) from ethyl acetate.

M.W. 360.438. m.p.: 217°–9° C. HPLC: 99.5% PMR: Consistent with structure. M.S.: M+H=361 (FAB). TLC: $R_f$=0.31, Silica GF (3:1 of ethyl acetate: $CH_2Cl_2$). CHN: Calc'd as $C_{23}H_{24}N_2O_2$: C, 76.64; H, 6.71; N, 7.77. Found: C, 76.26; H, 6.80; N, 7.76.

EXAMPLE 3

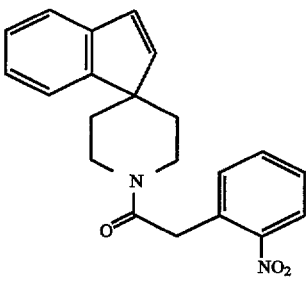

125 mg (0.564 mmol) of spiro(1H-indene-1,4'-piperidine) hydrochloride was dissolved in 3 ml DMF and the solution treated with 112 mg (0.620 mmol) of o-nitrophenyl acetic acid followed by 286 mg (0.649 mmol) of benzotriazol-1-yl-oxytris-(dimethylamino)-phosphonium hexafluorophosphate (BOP reagent). The pH of the solution was adjusted m 9.5 with 307 μl (1.75 mmol) of diisopropyl ethylamine and the mixture stirred at 25° C. for 1 hour.

DMF was removed in vacuo and the crude residue treated with $H_2O$ and extracted with ethyl acetate (3×). The organic extracts were combined, washed with water (1×), brine (1×), dried over $Na_2SO_4$, filtered and stripped to dryness in vacuo. Flash chromatography of the crude product on silica gel (3% $Et_2O$ in $CH_2Cl_2$) gave 155.7 mg (79.4% yield) of the title compound as a white foam after evaporation in vacuo.

M.W.: 348.386. m.p.: 60°–75° C. (sinter). HPLC: 93.4%. PMR: Consistent with structure plus water. M.S.: M+H=349.2 (FAB). TLC: $R_f$=0.29, Silica GF (4% $Et_2O$ in $CH_2Cl_2$). CHN: Calc'd as $C_{21}H_{20}N_2O_3 \cdot 0.30\ H_2O$ (F.W.=353.8): C, 71.28; H, 5.87; N, 7.92. Found: C, 71.35; H, 5.64; N, 7.91.

EXAMPLE 4

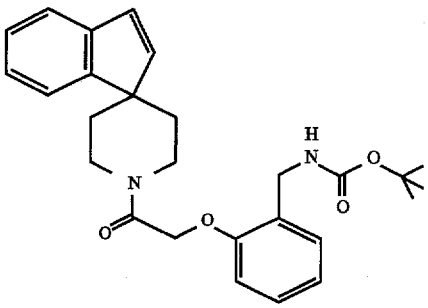

250 mg (1.13 mmol) spiro(1H-indene-1,4'-piperidine) hydrochloride was dissolved in 10 ml DMF and the solution treated with 350 mg (1.24 mmol) of 2-(t-butyloxyaminomethyl)-phenylacetic acid followed by 575 mg (1.30 mmol) of benzotriazol-1-yloxytris (dimethylamino)phosphonium hexafluorophosphate (BOP Reagent). The pH of the solution was adjusted to 9.5 with diisopropylethylamine and the mixture stirred at 25° C. for 1 hour.

DMF was removed in vacuo and the crude residue treated with water and extracted with ethyl acetate (3×). The organic extracts were combined, washed with water (1×), brine (1×), dried over $Na_2SO_4$, filtered and stripped to dryness in vacuo. Flash chromatography of the crude product on silica gel (13% $Et_2O$ in $CH_2Cl_2$) gave the title compound isolated as a crystalline solid (285 mg, 56% yield) from diethyl ether.

M.V.: 448.542. m.p.: 165°–7° C. HPLC: 97.2%. PMR: Consistent with structure plus ether. M.S.: M+H+ Thioglycerol (M.W.=108)=5573 (FAB). TLC: $R_f$=0.48, Silica GF (20% $ET_2O$ in $CH_2Cl_2$). CHN: Calc'd as $C_{27}H_{32}N_2O_4 \cdot 0.10\ C_4H_{10}O$ (F.W.=455.954) C, 72.17; H, 7.30; N, 6.14. Found: C, 72.12; H, 7.33; N, 6.29.

EXAMPLE 5

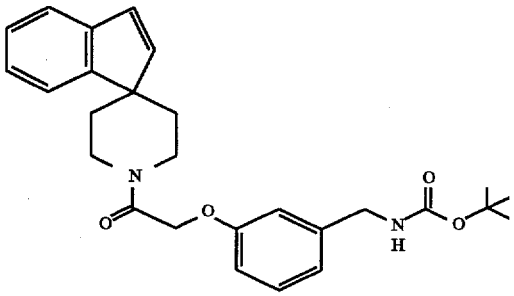

250 mg (1.13 mmol) of spiro(1H-indene-1,4'-piperidene) hydrochloride was dissolved in 10 ml DMF and the solution treated with 350 mg (1.24 mmol) of 3-(t-butyloxyaminomethyl)-phenyl acetic acid followed by 575 mg (1.30 mmol) of benzotriazol-1-yloxytris (dimethylamino)phosphonium hexafluorophosphate (BOP Reagent). The pH of the solution was adjusted to 9.5 with 550 µl (3.14 mmol) of diisopropylethylmine and the mixture stirred at 25° C. for 1 hour.

DMF was removed in vacuo and the crude residue treated with water and extracted with ethyl acetate (3×). The organic extracts were combined, washed with water (1×), dried over $Na_2SO_4$, filtered, and stripped to dryness in vacuo. Flash chromatography of the crude product on silica gel (20% $Et_2O$ in $CH_2Cl_2$) gave the title compound as a white foam (328 mg, 65.0% yield) upon coevaporation with ether (3×) in vacuo.

M.W.: 448.542. m.p.: 55°–72° C. (sinter). HPLC: 99.6% PMR: Consistent with structure plus water. M.S.: M+H+ Thioglycerol (M.W.=108)=557.6 (FAB). TLC: $R_f$=0.52, Silica GF (25% $Et_2O$ in $Ch_2Cl_2$). CHN: Calc'd as $C_{27}H_{32}N_2O_4$·0.15 $H_2O$ (F.W.=451.269): C, 71.86; H, 7.21; N, 6.21. Found: C, 71.83; H, 7.09; N, 6.45.

EXAMPLE 6

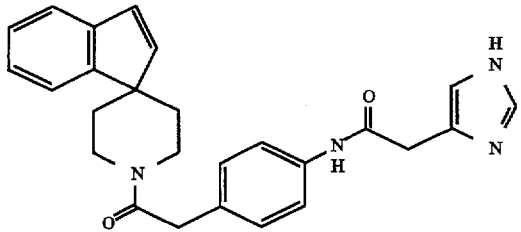

70 mg (0.220 mmol) of the product of Example 1 was dissolved in 5 ml DMF and the solution treated with 39.3 mg (0.242 mmol) of imidazole-4-acetic acid-hydrocloride followed by 32.7 mg (0.242 mmol) of 1-hydroxybenzotriazole hydrate (HBT) and 46.4 mg (0.242 mmol) of 1-ethyl-3-(3-dimethylaminopropyl)-carbodiimidehydrochloride (EDC). The pH was adjusted to 9.5 with triethylamine and the mixture stirred at 25° C. or 4 hours.

DMF was removed in vacuo and the crude residue treated with water and extracted with ethyl acetate (3×). The organic extracts were combined, washed with water (1×), brine (1×), dried over $Na_2SO_4$, filtered and stripped to dryness in vacuo. Flash chromatography of the crude product on silica gel (100:10:1 of $CH_2Cl_2$:MeOH: Conc $NH_4OH$) gave the title compound as a white solid (50.8 mg, 54.2% yield) after evaporation in vacuo and trituration with ether.

M.W.: 426.50. m.p.: 104°–36° C. (sinter). HPLC: 99.3% PMR: Consistent with structure plus ether, $CH_2Cl_2$, and water. M.S.: M+H+427.1 (FAB). TLC: $R_f$=0.32, Silica GF (80:10:1 of $CH_2Cl_2$:MeOH: Conc. $NH_4OH$). CHN: Calc'd a $C_{26}H_{26}N_4$)2·0.10 $CH_2Cl_2$·0.10: $C_4H_{10}O$·0.50 $H_2O$ (F.W.= 451.212): C, 70.53; H, 6.26; N, 12.42. Found: C, 70.56; H, 6.04; N, 12.64.

EXAMPLE 7

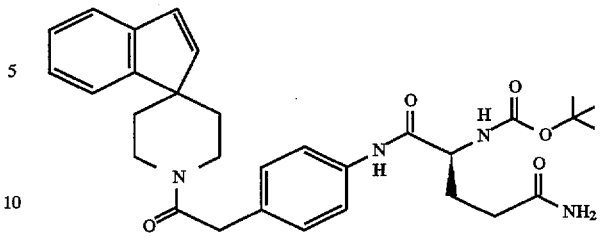

85 mg (0.267 mmol) of the product of Example 1 was dissolved in 5 ml DMF and the solution treated with 72.3 mg (0.294 mmol) of N-t-butyloxycarbonyl-L-glutamine followed by 39.7 mg (0.294 mmol) of 1-hydroxybenzotriazole hydrate (HBT) and 56.3 mg (0.294 mmol of 1-ethyl-3-(3-dimethylaminopropyl)carbodiimide hydrochloride (EDC). The pH was adjusted to 9.5 with 55 µl (0.395 mmol) of triethylamine (Et3N) and the mixture stirred at 25° C. for 1.5 hours.

A second portion of 72.3 mg (0.294 mmol) of N-t-butyloxycarbonyl-L-glutamine, 39.7 mg (0.294 mmol) of HBT, 56.3 mg (0.294 mmol) of EDC and 55 µl (0.395 mmol) of $Et_3N$ was added and the mixture stirred at 25° C. for 18 hours.

DMF was removed in vacuo and the residue treated with $H_2O$ and extracted with ethyl acetate (3×). The organic extracts were combined, washed with water (1×), brine (1×), dried over $Na_2SO_4$, filtered and stripped to dryness in vacuo. Flash chromatography of the crude product on silica gel (6% MeOH in $CH_2Cl_2$) gave the title compound as a white solid (57.4 mg, 39.3% yield) after evaporation in vacuo and trituration with ether.

M.W.: 546.646. m.p.: 104°–47° C. (sinter). HPLC: 99.1%. PMR: Consistent with structure plus water and ether. M.S.: M+H=547 (FAB). TLC: $R_f$=0.18, Silica GF (4% MeOH in $CH_2Cl_2$). CHN: Calc'd as $C_{31}H_{38}N_4O_5$·0.10 $C_4H_{10}O$·0.75 $H_2O$ (F.W.=5657.597): C, 66.44; H, 7.19; N, 9.87. Found: C, 66.42; H, 6.98; N, 10.04.

EXAMPLE 8

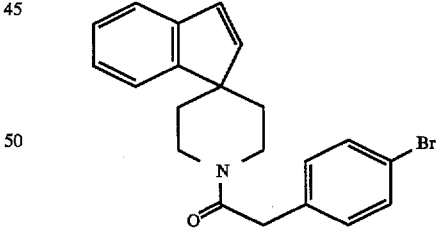

75 mg (0.338 mmol) of spiro(1H-indene-1,4'-piperidine) hydrochloride was dissolved in 3 ml DMF and the solution treated with 80.0 mg (0.372 mmol) of 4-bromophenyl acetic acid followed by 171.9 mg (0.389 mmol) of benzotriazol-1-yloxytris(dimethylamino)-phosphonium hexafluorophosphate (BOP Reagent). The pH of the solution was adjusted to 9.5 with 125 ml (0.710 mmol) of diisopropylethylamine and the mixture stirred at 25° C. for 1 hour.

DMF was removed in vacuo and the crude residue treated with water and extracted with ethyl acetate (3×). The organic extracts were combined, washed with water (1×), brine (1×), dried over $Na_2SO_4$, filtered and stripped to dryness in vacuo.

Flash chromatography of the crude product on silica gel (5% Et₂O in CH₂Cl₂) gave the title compound as a white foam (30 mg, 23.3 % yield) upon coevaporation with ether (3×) in vacuo.

M.W.:=382.282. m.p.: 44°–58° C. (sinter). HPLC: 99.5%. PMR: Consistent with structure plus water. M.S.: M+H= 382.1/384.1 at 1/1 (FAB). TLC: $R_f$=0.44, Silica GF (6% Et₂O in Ch₂Cl₂). CHN: Calc'd as $C_{21}H_{20}BrNO \cdot 0.40 \ H_2O$ (F.W.=389.513): C, 64.75; H, 5.38; N, 3.60. Found: C, 64.51; H, 5.06; N, 3.60.

EXAMPLE 9

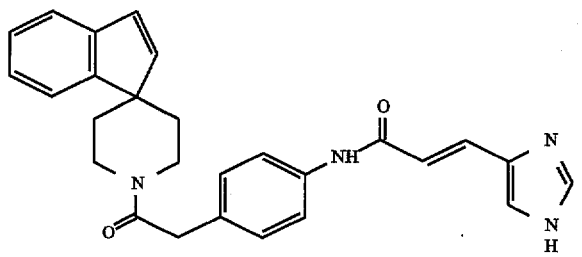

375 mg (1.18 mmol) of the product of Example 1 was dissolved in 10 ml DMF and the solution treated with 179 mg (1.30 mmol) of urocanic acid followed by 175 ml (1.29 mmol of 1-hydroxybenzotriazole hydrate (HBT) and 248.5 mg (1.30 mmol) of 1-ethyl-3-(3-dimethyl-aminopropyl) carbodiimide hydrochloride (EDC). The pH of the solution was adjusted to 9.5 with 414 µl (0.298 mmol) of triethylamine (Et₃N) and the reaction stirred at 25° C. for 6 hours.

A second portion consisting of 179 mg (1.30 mmol) of urocanic acid, 175 mg (1.29 mmol) of HBT, 249 (1.30 mmol) of EDC and 414 µl (0.298 mmol) of Et₃N was added and the reaction stirred at 25° C. for 18 hours.

DMF was removed in vacuo and the residue treated with water and extracted with ethyl acetate (3×). The organic extracts were combined, washed with water (1×), brine (1×), dried over Na₂SO₄, filtered and stripped to dryness in vacuo. Flash chromatography of the crude product on silica gel (100:10:1 of CH₂Cl₂:MeOH: Conc. NH₄OH) gave the title compound as a crystalline solid (106 mg, 20.5% yield) from ethyl acetate.

M.W.:=438.51. m.p.: 170°–85° C. (Physical Change); 228°–30° C. (melt). HPLC: 99.0%. PMR: Consistent with structure plus water. M.S.: M+H=439 (FAB). TLC: $R_f$=0.36, silica GF (80:10:1 of CH₂Cl₂:MeOH: Conc. NH₄OH). CHN: Calc'd as $C_{27}H_{26}N_4O_2 \cdot 0.95 \ H_2O$ (F.W.455.468): C, 71.17; H, 6.17; N, 12.30. Found: C, 71.05; H, 5.78; N, 11.91.

EXAMPLE 10

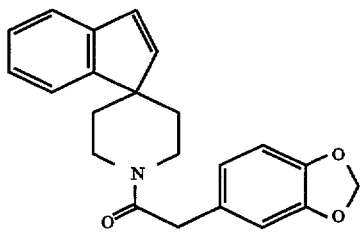

60 mg (0.271 mmol) of spiro(1H-indene-1,4'-piperidine) hydrochloride was dissolved in 4 ml DMF and the solution treated with 53.7 mg (0.298 mmol) of 3,4-methylenedioxy phenyl acetic acid followed by 137.8 mg (0.312 mmol) of benzotriazol-1-yloxytris (dimethylamino) phosphonium hexafluorophosphate (BOP Reagent). The pH of the solution was adjusted to 9.5 with 100 µl (0.569 mmol) of diisopropylethylamine and the mixture stirred at 25° C. for 1 hour.

DMF was removed in vacuo and the crude residue treated with water and extracted with ethyl acetate (3×). The organic extracts were combined, washed with water (1×), brine (1×), dried over Na₂SO₄, filtered and stripped to dryness in vacuo. Flash chromatography of the crude product on silica gel (6% Et₂O in CH₂Cl₂) gave the title compound as a crystalline solid (32.4 mg, 34.3% yield) from ether.

M.W.: 347.396. m.p.: 123°–5° C. HPLC: 99.4% PMR: Consistent with structure plus water. M.S.: M+H=348.1 (FAB). TLC: $R_f$=0.30, Silica GF (6% Et₂O in Ch₂Cl₂) CHN: Calc'd as $C_{22}H_{21}NO_3 \cdot 0.15 \ H_2O$ (F.W.=350.119): C, 75.47; H, 6.13; N, 4.00. Found: C, 75.51; H, 5.79; N, 4.01.

EXAMPLE 11

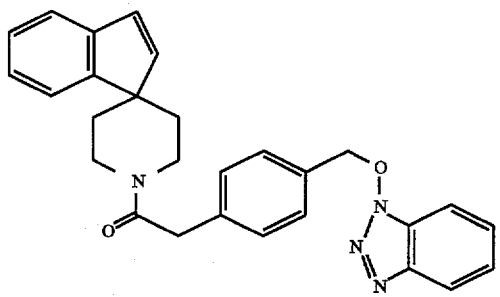

300 mg (1.35 mmol) of spiro(1H-indene-1,4'-piperidine) hydrochloride was dissolved in 10 ml DMF and the solution treated with 341 mg (1.49 mmol) of p-bromoethyl phenyl acetic acid followed by 687 mg (1.55 mmol) of benzotriazol-1-yloxy(dimethylamino) phosphonium hexafluorophosphate (BOP Reagent). The pH of the solution was adjusted to 9.5 with 769 µl (4.39 mml) of diisopropylethylamine and the mixture stirred at 25° C. for 18 hours.

DMF was removed in vacuo and the crude residue treated with water and extracted with ethyl acetate (3×). The oganic extracts were combined, washed with water (1×), brine (1×), dried over Na₂SO₄, filtered and stripped to dryness in vacuo. Flash chromatography of the crude product on silica gel (12% Et₂O in CH₂Cl₂) gave the title compound as a white foam (318 mg, 59.3% yield) upon coevaporation with ether (3×) in vacuo.

M.W.: 450.52. m.p.: 50°–64° C. HPLC: 94.9%. PMR: Consistent with structure plus water. M.S.: M+H=451 (FAB). TLC: $R_f$=0.27, silica GF (15% Et₂O in CH₂Cl₂). CHN: Calc'd as $C_{28}H_{26}N_4O_2 \cdot 1.30 \ H_2O$ (F.W.=473.965): C, 70.95; H, 6.08; N, 11.82. Found: C,70.98; H, 5.81; N, 12.00.

EXAMPLE 12

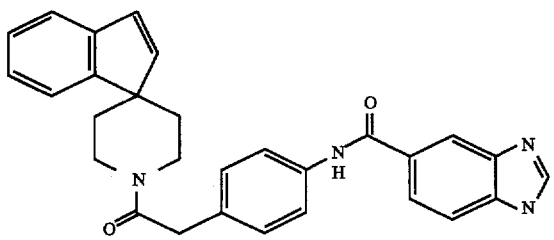

60 mg (0.188 mmol) of the product of Example 1 was dissolved in 3 ml DMF and the solution treated with 36.6 mg (0.226 mmol) of benzoimidazole-5-carboxylic acid followed by 30.5 mg (0.226 mmol) of 1-hydroxybenzotriazole hydrate (HBT) and 43.3 mg (0.226 mmol) of 1-ethyl-3-(3-dimethylaminopropyl)-carbodiimide hydrochloride (EDC). The pH was adjusted to 9.5 with 63.0 µl (0.453 mmol) of triethylamine and the mixture stirred at 25° C. for 20 hours.

A second portion consisting of 18.3 mg (0.226 mmol) of benzoimidazole-5-carboxylic acid, 15.3 mg (0.113 mmol) HBT, 21.7 mg (0.113 mmol) EDC and 31.5 µl (0.227 mmol) of triethylamine was added and the reaction stirred at 25° C. for 6 hours.

DMF was removed in vacuo and the residue treated with water and extracted with ethyl acetate (3×). The organic extracts were combined, washed with water (1×), brine (1×), dried over $Na_2SO_4$, filtered and stripped to dryness in vacuo. Flash chromatography of the crude product on silica gel (100:10:1 of $CH_2Cl_2$:MeOH: Conc. $NH_4OH$) gave the title compound as a crystalline solid (5.15 mg, 59.1% yield) from ethyl acetate.

M.W.: 462.53. m.p.: 212°–6° C. HPLC: 98.8%. PMR: Consistent with structure. M.S.: M+H=463 (FAB). TLC: $R_f$=0.34, silica GF (80:10:1 of $Cl_2$:MeOH:Conc $NH_4OH$). CHN: Calc'd as $C_{29}H_{26}N_4O_2$: (m.w.–462.53): C, 75.30; H, 5.67; N, 12.11. Found: C, 75.18; H, 5.66; N, 12.06.

EXAMPLE 13

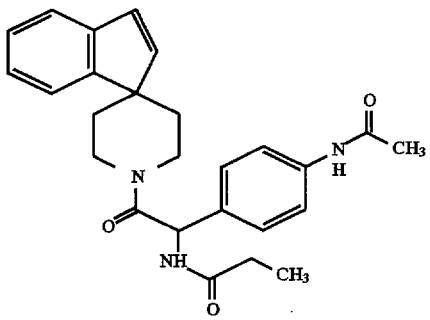

100 mg (0.451 mmol) of spiro(1H-indene-1,4'-piperidine) hydrochloride was dissolved in 3 ml DMF N-ethoxycarbonyl-α-(4-Acetamidophenyl)-glycine followed by 229 mg (0.519 mmol) of benzotriazol-1-yl-oxytris (dimethylamino)phosphonium hexafluorophosphate (BOP Reagent). The pH of the solution was adjusted to 9.5 with 166 µl (0.947 mmol) of diisopropylethylamine and the mixture stirred at 25° C. for 1 hours.

DMF was removed in vacuo and the crude residue treated with water and extracted with ethyl acetate (3×). The organic extracts were combined, washed with water (1×), brine (1×), dried over $Na_2SO_4$, filtered and stripped to dryness in vacuo. Flash chromatography of the crude product on silica gel (3% MeOH in $CH_2Cl_2$) gave the title compound isolated as a crystalline solid (139 mg, 68.8% yield) from ether.

M.W.: 447.516. m.p.: 216°–8° C. HPLC: 98.1%. PMR: Consistent with structure. M.S.: M+H=448.1 (FAB). TLC: $R_f$=0.27, silica GF (4% MeOH in $CH_2Cl_2$). CHN: Calc'd as $C_{26}H_{29}N_3O_4$ (F.W. –447.516): C, 69.78; H, 6.53; N, 9.39. Found: C, 69.67; H, 6.51; N, 9.55.

EXAMPLE 14

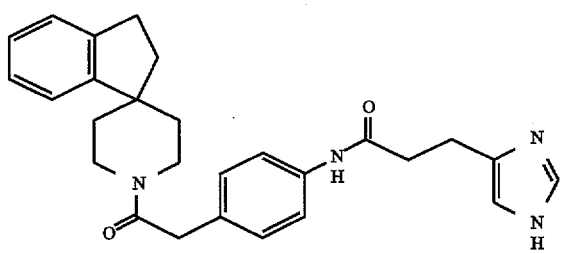

74.4 mg (0.170 mmol) of the product of Example 9 was dissolved in 10 ml of absolute ethanol, treated with 15 mg 10% Pd on C under a nitrogen atmosphere, and hydrogenated at 60 psi for 3 hours. The mixture was filtered through Solka Floc® to remove catalyst and the filter pad was washed thoroughly with fresh absolute ethanol. The filtrate was evaporated to dryness in vacuo and the residue was flash chromatographed on silica gel (60:10:1 of $CH_2Cl_2$:MeOH:$H_2O$:HoAc). The product fractions were combined, stripped to dryness in vacuo, and the residue treated with dilute NaHCO3(aq) and extracted with ethyl acetate (3×). The organic extracts were combined, washed with water (1×), dried over $Na_2SO_4$, filtered and stripped to dryness in vacuo. The residue was coevaporated with ether (3×), then triturated with ether and filtered to give the title compound as a white solid (44.8 mg, 59.7% yield).

M.W.: 442.542. m.p.: 89°–128° C. HPLC: 99.6%. PMR: Consistent with structure plus ether, ethyl acetate and water. M.S.: M+H=443.1 (FAB). TLC: $R_f$=0.29, silica GF (60:10:1:1 of $CH_2Cl_2$:MeOH:$H_2O$:HoAc). CHN: Calc'd as $C_{27}H_{30}N_4O_2 \cdot 0.15\ C_4H_{10}O \cdot 0.10\ C_4H_8O_2 \cdot 0.35\ H_2O$: C, 71.74; H, 7.10; N, 11.95. Found: C, 71.68; H, 7.05; N, 11.75.

EXAMPLE 15

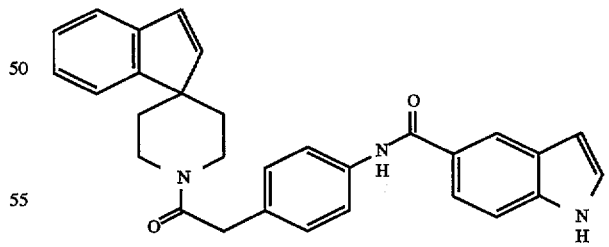

50 mg (0.157 mmol) of the product of Example 1 was dissolved in 2 ml DMF and the solution treated with 27.8 mg (0.173 mmol) of indole-5-carboxylic acid followed by 23.3 mg (0.173 mmol of 1-hydroxybenzotriazole hydrate (HBT) and 33.1 mg (0.173 mmol) of 1-ethyl-3-(3-dimethylaminopropyl)-carbodiimide hydrochloride (EDC). The pH of the solution was adjusted to 9.5 with 49 µl (0.350 mmol) of triethylamine and the reaction stirred at 25° C. for 1 hour.

A second portion consisting of 13.0 mg (0.081 mmol) of indole-5-carboxylic acid, 12.0 mg (0.089 mmol) HBT, 15.0 mg (0.078 mmol) EDC, and 22.1 μl (0.159 mmol) of triethylamine was added and the reaction stirred at 25° C. for 1 hour. DMF was removed in vacuo and the residue treated with water and extracted with ethyl acetate (3×). The organic layers were combined, washed with water (1×), brine (1×), dried over Na$_2$SO$_4$, filtered and stripped to dryness in vacuo. Flash chromatography of the crude product on silica gel (230:10:1 of CH$_2$Cl$_2$:MeOH:Conc. NH$_4$OH) gave the title compound as an off-white solid (30.0 mg, 37.6% yield) upon trituration with ethyl acetate.

M.W.: 461.54. m.p.: 241°–3° C. HPLC: 97.7%. PMR: Consistent with structure plus water. M.S.: M+H=462 (FAB). TLC: R$_f$=0.25, silica GF (200:10:1 of CH$_2$Cl$_2$:MeOH:conc. NH$_4$OH) CHN: Calc'd as C$_{30}$H$_{27}$N$_3$O$_2$·0.75 H$_2$O. (F.W.=492.701): C, 75.08; H, 6.16; N, 8.53. Found: C, 74.97; H, 5.80; N, 8.47.

EXAMPLE 16

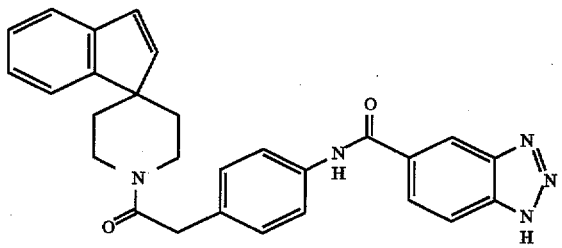

55 mg (0.173 mmol) of the product of Example 1 was dissolved in 2 ml DMF and the solution was treated with 33.9 mg (0.208 mmol) of benzotriazole-5-carboxylic acid followed by 28.1 mg (0.208 mmol) of 1-hydroxybenzotriazole hydrate (HBT) and 39.9 mg (0.208 mmol of 1-ethyl-3-(3-dimethylaminopropyl)-carbodiimide hydrochloride (EDC). The pH of the solution was adjusted to 9.5 with 66.6 μl (0.478 mmol) of triethylamine and the reaction stirred at 25° C. for 18 hours.

DMF was removed in vacuo and the residue treated with water and extracted with ethyl acetate (3×). The organic extracts were combined, washed with water (1×), brine (1×), dried over Na$_2$SO$_4$, filtered and stripped in dryness in vacuo. Flash chromatography of the crude product on silica gel (88:10:1 of CH$_2$Cl$_2$:MeOH: Conc. NH$_4$OH) gave the title compound as a crystalline solid (39.8 mg, 49.8% yield from ethyl acetate.

M.W.: 463.52. m.p.: 229°–32° C. HPLC: 99.6% PMR: Consistent with structure plus ethyl acetate. M.S.: M+H= 464 (FAB). TLC: R$_f$=0.33, silica GF (80:10:1 of CH$_2$Cl$_2$:MeOH:Conc. NH$_4$OH) CHN: Calc'd as C$_{28}$H$_{25}$N$_5$O$_2$·0.05 C$_4$H$_8$O$_2$ (F.W.=467.948): C, 72.38; H, 5.47; N, 14.97. Found: C, 72.39; H, 5.33; N, 14.92.

EXAMPLE 17

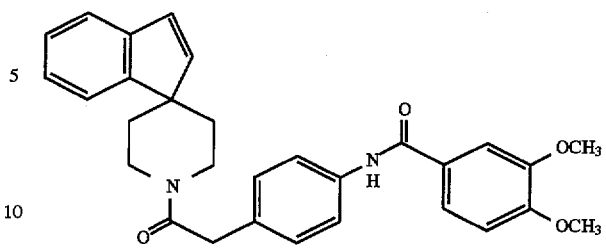

55.0 mg (0.173 mmol) of the product of Example 1 was dissolved in 3 ml CH$_2$Cl$_2$ and the solution treated with 37.9 mg (0.189 mmol) of 3,4-dimethoxybenzoyl chloride. The pH of the solution was adjusted to 9.5 with 28.0 μl (0.201 mmol) of triethylamine and the mixture stirred at 25° C. for 15 minutes. Flash chromatography of the reaction mixture directly on silica gel (40% Et$_2$O in CH$_2$Cl$_2$) gave the title compound as a white solid (20.0 mg, 24.0% yield) upon trituration with ether.

M.W.: 482.556. m.p.: 107°–18° C. (shrink). HPLC: 99.6%. PMR: Consistent with structure plus ether and water. M.S.:=M+H=483 (FAB). TLC: R$_f$=0.26, silica GF (40% Et$_2$O in CH$_2$Cl$_2$). CHN: Calc'd as C$_{30}$H$_{30}$N$_2$O$_4$·0.15 C$_4$H$_{10}$O·0.35 H$_2$O (F.W.=500.008): C, 73.50; H, 6.49; N, 5.60. Found: C, 73.48; H, 6.31; N, 5.55.

EXAMPLE 18

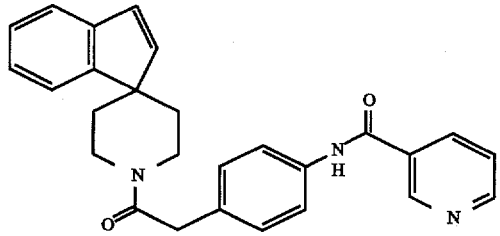

60 mg (0.188 mmol) of the product of Example 1 was dissolved in 2 ml CH2CL2 and the solution treated with 36.9 mg (0.207 mmol) of nicotinoylchloride hydrochloride. The pH of the mixture was adjusted to 9.5 with 58 μl (0.416 mmol) of triethyl amine and the reaction stirred at 25° C. for 18 hours.

Flash chromatography of the reaction mixture directly on silica gel (4% MeOH in CH$_2$Cl$_2$) gave the title compound as a white solid (56.8 mg, 71.3% yield) crystallized from ether.

M.W.: 423.494. m.p.: 205°–6° C. HPLC: 99.7%. PMR: Consistent with structure. M.S.: M+H=424 (FAB). TLC: R$_f$=0.26, silica GF (5% MeOH in CH$_2$Cl$_2$). CHN: Calc'd as C$_{27}$H$_{25}$N$_3$O$_2$: C, 76.57; H, 5.92; N, 9.92. Found: C, 76.50; H, 5.90; N, 9.91.

EXAMPLE 19

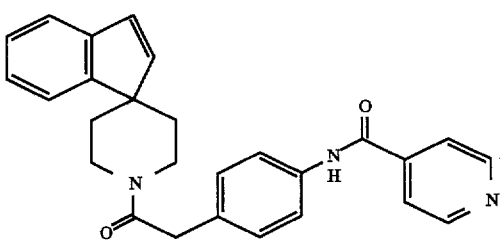

60 ml (0.188 mmol) of the product of Example 1 was dissolved in 2 ml $CH_2Cl_2$ and the solution treated with 36.9 mg (0.207 mmol) of isonicotinoyl chloride hydrocloride. The pH of the mixture was adjusted to 9.5 with 58 µl (0.416 mmol) of triethylamine and the reaction stirred at 25° C. for 1 hour.

Flash chromatography of the reaction mixture directly on silica gel (5% MeOH in $CH_2CL_2$) gave the title compound as a white solid (56.0 mg, 70.4% yield) crystallized from ether.

M.W.: 423.494. m.p.: 224°–6° C. HPLC: 99.7% PMR: Consistent with structure. M.S.: M+H=424 (FAB). TLC: $R_f$=0.23, silica GF (5% MeOH in $CH_2Cl_2$). C, 76.57; H, 5.92; N, 9.92. Found: C, 76.22; H, 5.95; N, 9.74.

TABLES

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in Table 1 below are with reference to the following generic structure:

TABLE 1

| X | R¹ |
|---|---|
| —CH₂— | (4-aminophenyl) |
| —CH₂— | (2-acetamidophenyl, H₃CCHN(O)—) |
| —CH₂— | (2-aminophenyl, H₂N—) |
| no substituent | (2-acetamidophenyl) |
| —CH₂— | (2-methoxybenzyl amine) |
| —CH₂— | (3-methoxybenzyl amine) |
| —CH₂— | H |
| —CH₂— | (4-isobutyramidophenyl) |
| —CH₂— | (3-methoxybenzyl acetamide) |
| —CH₂— | (2-methoxybenzyl acetamide) |
| —CH₂— | (4-Boc-aminomethylphenyl) |
| no substituent | (4-Boc-aminomethylphenyl) |
| —CH₂— | (3-aminophenyl) |
| —CH₂— | (3-acetamidophenyl) |

TABLE 1-continued
| X | R¹ |
|---|---|
| —CH₂— | 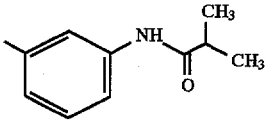 |
| —CH₂— | 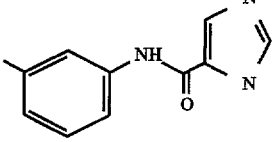 |
| —CH₂— | 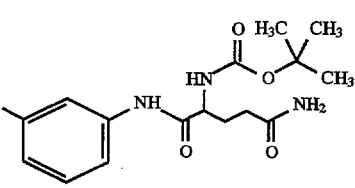 |
| no substituent | 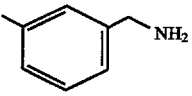 |
| —CH₂— | 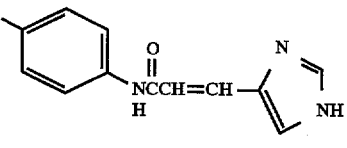 |
| no substituent | 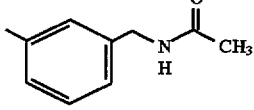 |
| —CH—<br> \|<br>CH₃ | 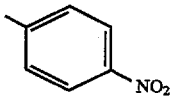 |
| no substituent | 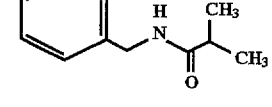 |
| —CH₂— | 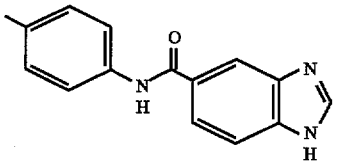 |
| —CH—<br> \|<br>CH₃ | 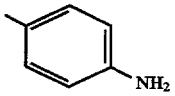 |
| —CH—<br> \|<br>CH₃ | 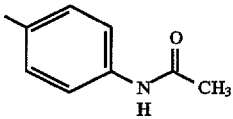 |
| —CH₂— | 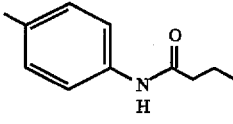 |
| —CH₂— |  |
| —CH₂— | 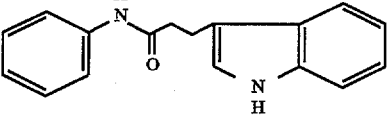 |
| —CH₂— | 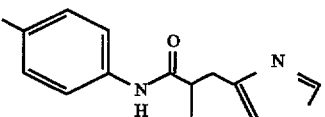 |
| —CH=CH— | 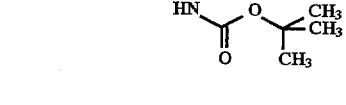 |
| —CH₂— | 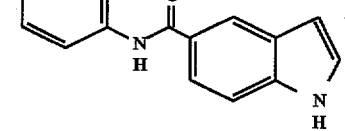 |

TABLE 2
The variables shown in Table 2 are with reference to the following structure:
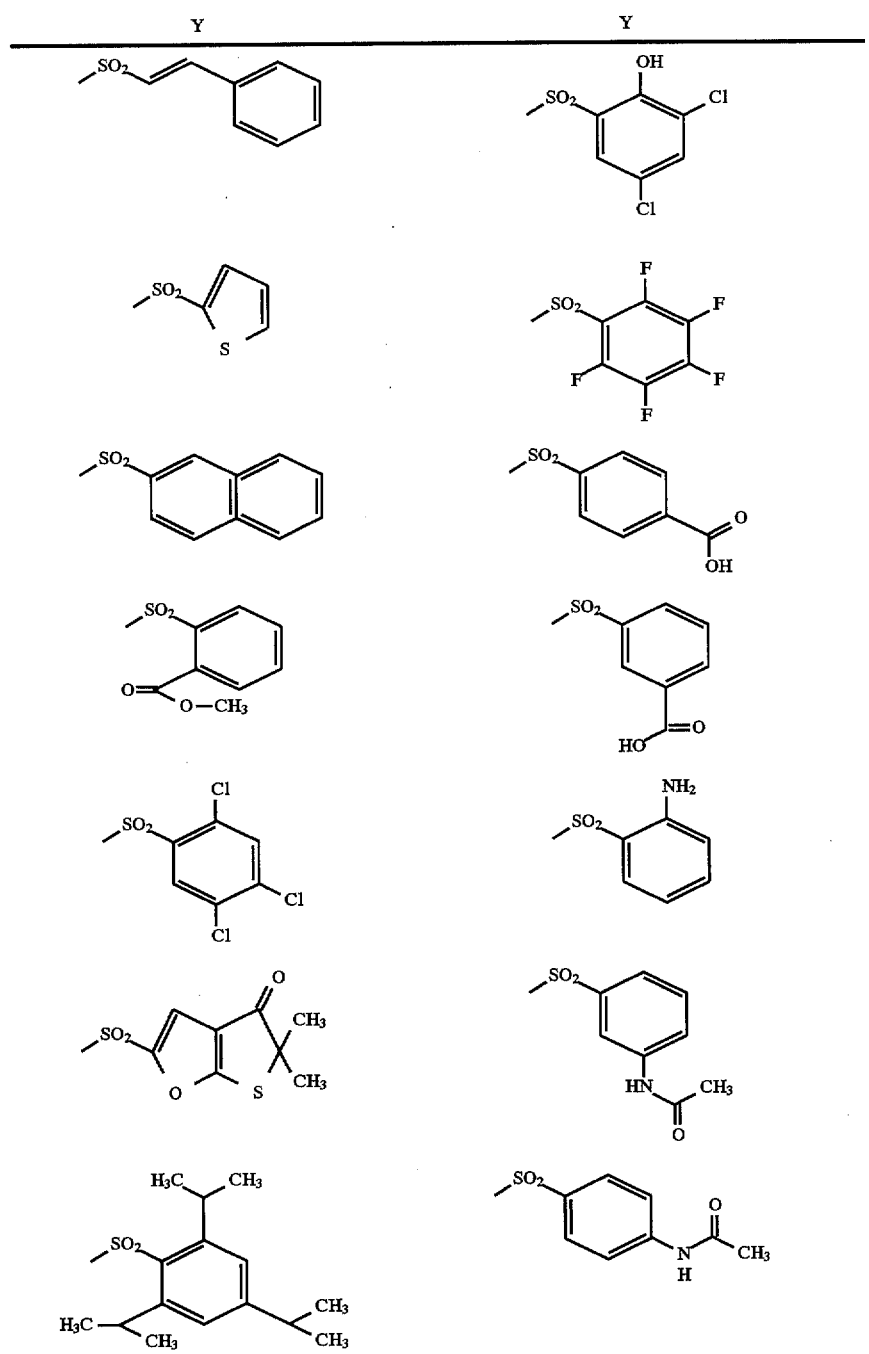

TABLE 2-continued
The variables shown in Table 2 are with reference to the following structure:
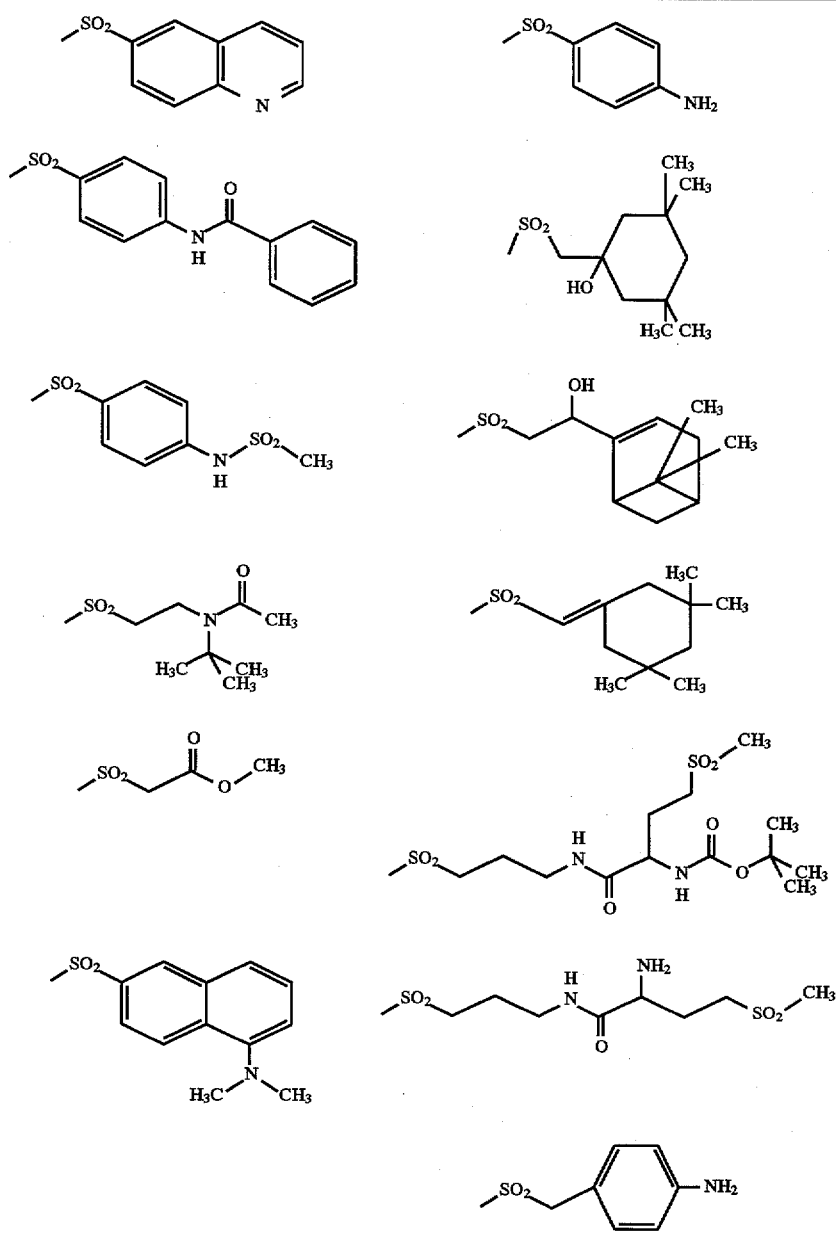

TABLE 2-continued
The variables shown in Table 2 are with reference to the following structure:
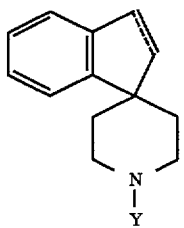
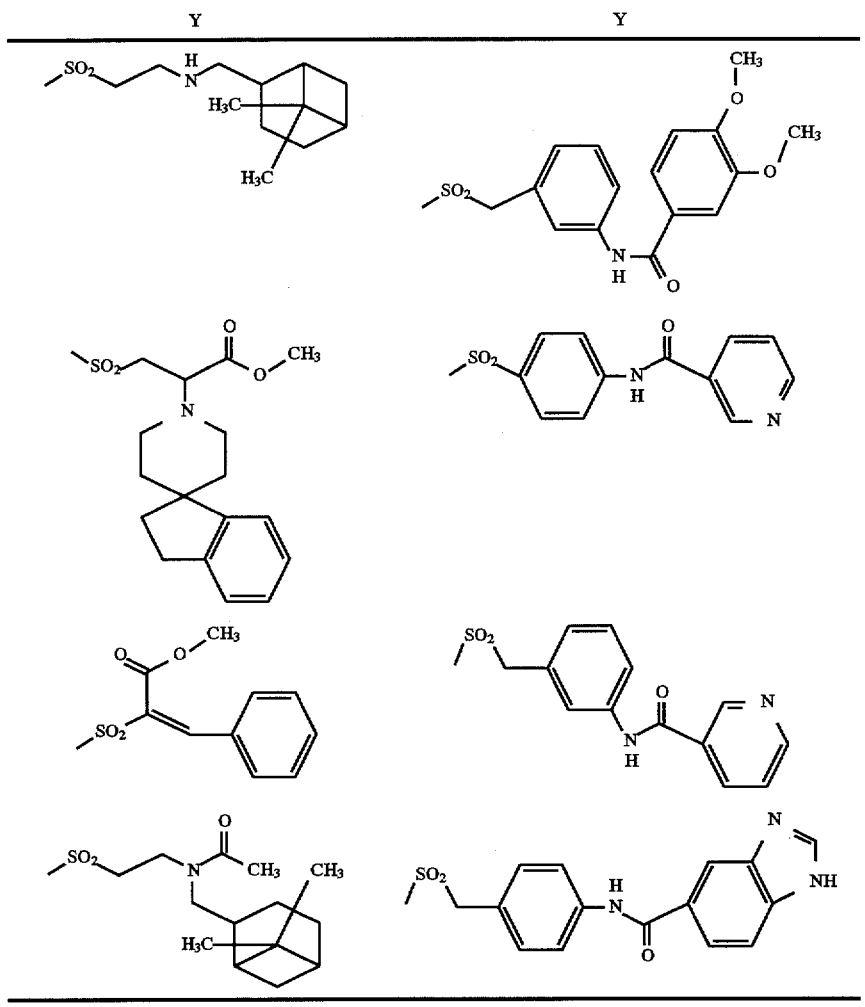

TABLE 3
The variables shown in Table 3 are with reference to the following structure:
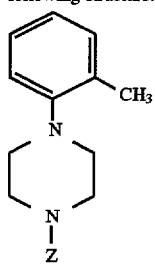
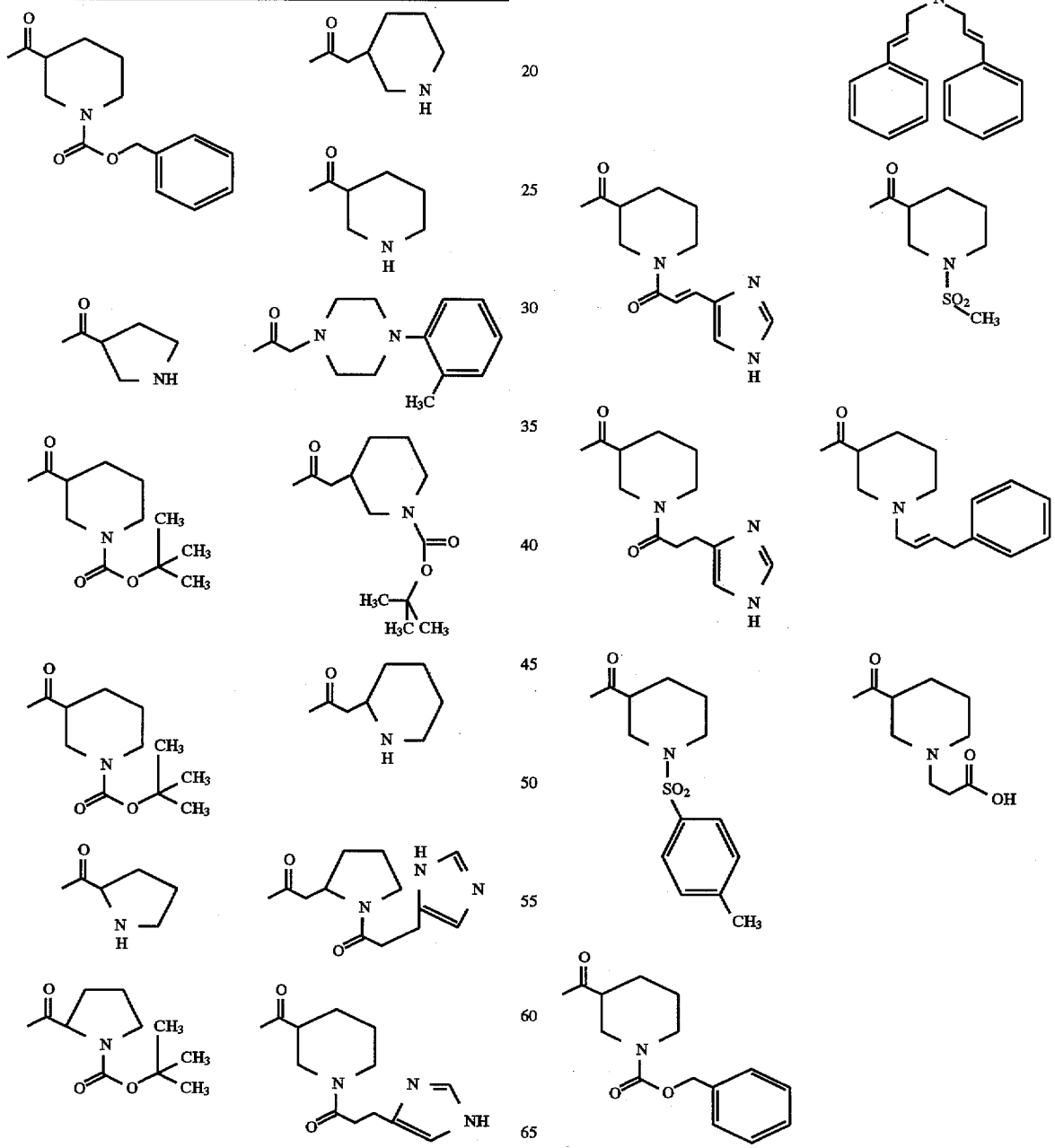
TABLE 3-continued
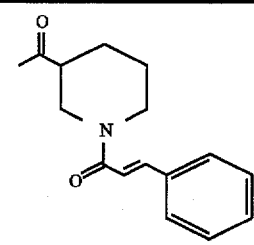
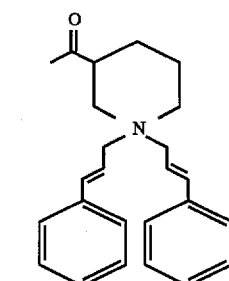
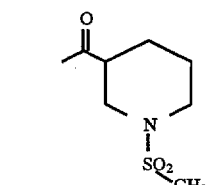
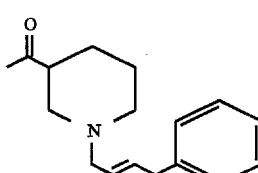
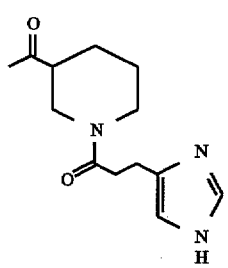
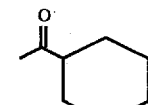
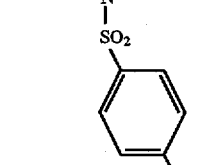
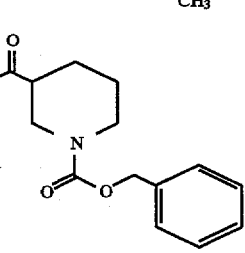

TABLE 3-continued

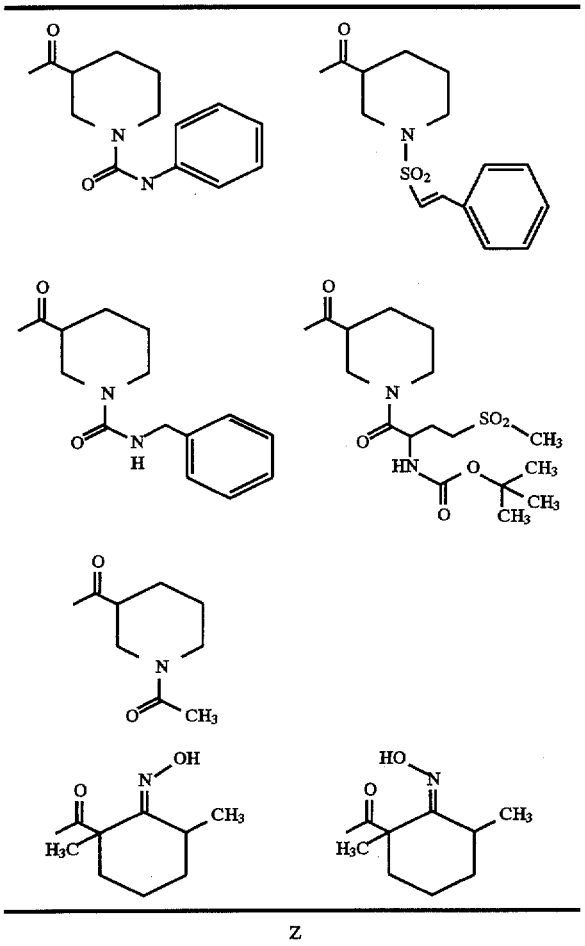

Z

TABLE 3-continued

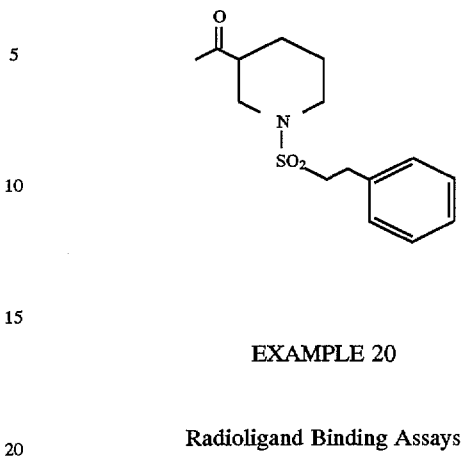

EXAMPLE 20

Radioligand Binding Assays

The high affinity binding of [$^3$H] Oxytocin (OT)([tyrosyl, 3,5-[$^3$H]OT; 30–60 Ci/mmol; New England Nuclear. Boston, Mass.) to uterine OT receptors was based on an assay (Fuchs, A-R; Fuchs, F; Soloff, MS. 1985 J. Clin. Endocrinol. Metab. 60:37) using a crude membrane preparation of uteri taken from diethylstilbestrol dipropionate (DES)-treated (0.3 mg/kg, ip; 18–24) rats. Competition studies were conducted at equilibrium (60 minutes; 22° C.) using 1 nM[$^3$H]OT in the following assay buffer: 50 mM Tris-HCl, 5 mM MgCl$_2$, and 0.1% BSA, pH 7.4. Nonspecific binding (10% of the total binding) was determined using 1 µM unlabeled OT and the binding reaction was terminated by filtration through glass fiber filters using a cell harvester (model 7019, Skatron, Inc., Sterling, Va.). IC$_{50}$ (the concentration of tested compound that inhibits 50% of OT) was reported, unless otherwise noted.

The measurement of [$^3$H]Vasopressin (AVP) ([phenylalanyl-3,4,5-$^3$H]AVP; 80–90 Ci/mmol; New England Nuclear)binding to a crude membrane preparation of male rat liver (AVP-V$_1$ sites) or kidney medulla (AVP-V$_2$ sites) was determined according to the method of Butlen, et al. (Butlen, D; Guillon, G; Rajerison, R. M.;Jard, S; Sawyer, W. H.;Manning, M. 1978 Mol Pharmacol 14:1006).

Competition assays were conducted at equilibrium (30 minutes at 30° C.) using 1 nM [$^3$H]AVP (liver) or 2 nM [$^3$H]AVP (kidney) in the following assay buffer: 100 mM Tris-HCl, 5 mM MgCl$_2$, 0.1% BSA, 50 mM phenylmethylsulfonylfluoride, and 50 mg/ml bacitracin, pH 8.0. Nonspecific binding (5–10% of the total binding) was determined using 10 µM unlabeled AVP, and the binding reaction was terminated by filtration as described above for the [$^3$H]OT binding assay.

IC$_{50}$ values were determined for both [$^3$H]OT and [$^3$H] AVP binding assays by linear regression of the relation log concentration of compound vs. percent inhibition of specific binding.

| Example | IC$_{50}$ [$^3$H]OT (nM) |
| --- | --- |
| 10 | 3,700 |
| 12 | 150 |
| 14 | 170 |
| 15 | 310 |
| 16 | 520 |

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth hereinabove may be applicable as a consequence of variations in the responsiveness of the mammal being treated for prevention of preterm labor, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

We claim:

1. A compound or a pharmaceutically acceptable salt thereof, of the formula X-Y-Z-R$^1$, wherein X is

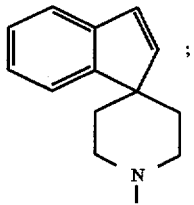

Y is —CO—, or —SO$_2$—;

Z is an optional substituent that, when present, is —NH—, —O—, —CHR—, —CH=CH—, —CH=, —(CH$_2$)$_m$— or —CHCHOH—;

R is C$_{1-5}$ alkyl or C$_{1-5}$ alkoxycarbonylamino,

R$^1$ is —CH$_3$, —CH(CH$_3$)$_2$, —NR$^4$R$^5$, —NCOR$^6$ or

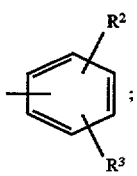

R$^2$ is acetyl, O-Het where Het is imidazole or benzimidazole or azimidobenzene, or where R$^2$ is further defined as —COR$^6$, —(CH$_2$)$_m$— NHCOR$^7$, —(CH$_2$)$_m$—NHCOOR$^7$, —(CH$_2$)$_m$—NR$^8$R$^9$, —(CH$_2$)$_m$—NHCO—(CH$_2$)$_m$R$^7$, —(CH$_2$)$_m$—NHCO—CHR$^7$R$^7$, —(CH$_2$)$_m$—NHCO—CH=CHR$^7$, —NHSO$_2$R— where R is as defined above, NHSO$_2$R$^7$, —SO$_2$R$^{10}$, —COR$^{11}$,

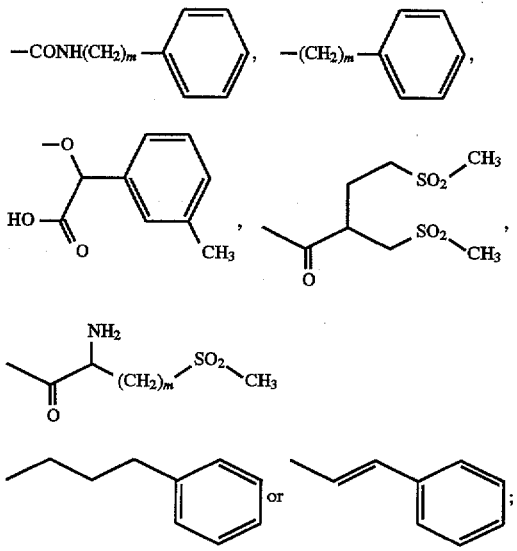

R$^3$ is hydrogen, or hydroxyl;

R$^4$ is hydrogen, C$_{1-5}$ alkyl, or C$_{6-10}$ cycloalkyl;

R$^5$ is hydrogen or acetyl;

R$^6$ is

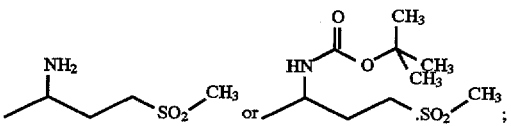

R$^7$ is

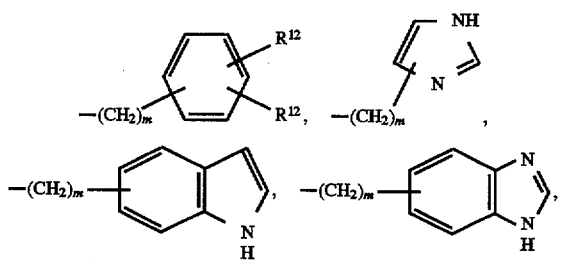

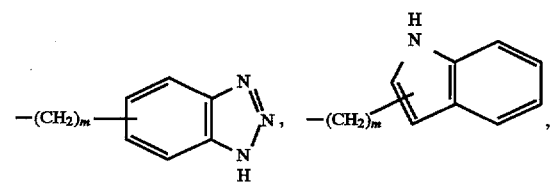

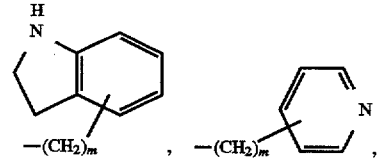

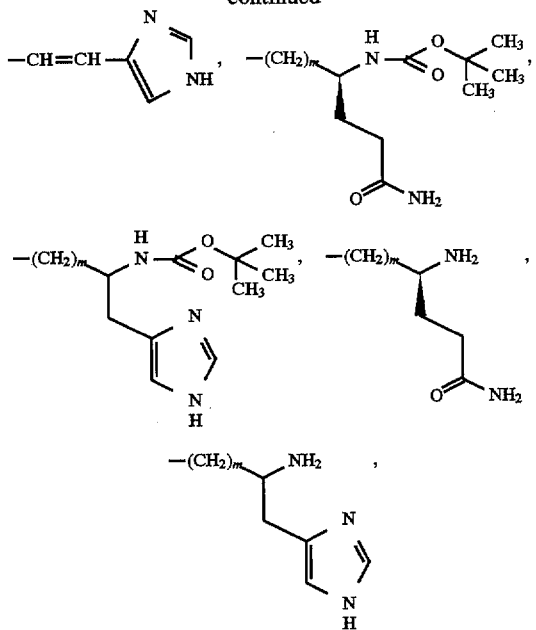

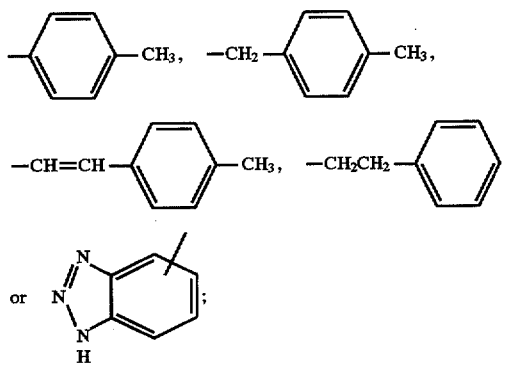

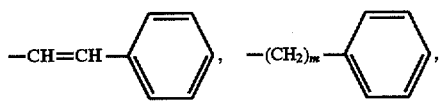

hydrogen, $C_{1-4}$ alkyl, $NSO_2R^{12}$ or $NHO-C_{1-4}$ alkyl;

$R^8$ is hydrogen or $C_{1-5}$ alkyl;

$R^9$ is hydrogen or $C_{1-5}$ alkyl;

$R^{10}$ is $-CH_3$,

[structures]

$R^{11}$ is $-CH_3$,

[structures]

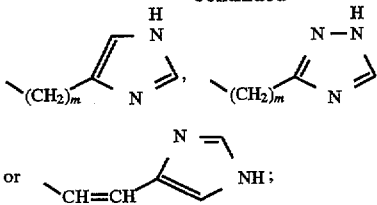

$R^{12}$ is hydrogen, $C_{1-5}$ alkyl or $C_{1-5}$ alkoxy; and m is an integer of from 0 to 5.

2. A pharmaceutical composition comprising a pharmaceutically acceptable carrier and a pharmacologically effective amount of the compound as claimed in claim 1 sufficient to prevent preterm labor in a mammal in need thereof.

3. A method of antagonizing oxytocin from binding to its receptor site in a mammal, comprising the step of administering to said mammal a pharmacologically effective amount of the compound as claimed in claim 1.

4. A method of preventing preterm labor in a mammal in need thereof, comprising the step of administering to said mammal a pharmacologically effective amount of the compound as claimed in claim 1.

5. A method stopping labor preparatory to cesarian delivery in a mammal in need thereof, comprising the step of administering to said mammal a pharmacologically effective amount of the compound as claimed in claim 1.

6. A method of treating dysmenorrhea in a mammal in need thereof, comprising the step of administering to said mammal a pharmacologically effective amount of the compound as claimed in claim 1.

7. A method of antagonizing vasopressin from binding to its receptor site in a mammal, comprising the step of administering to said mammal a pharmacologically effective amount of the compound as claimed in claim 1.

8. A method of inducing vasodilation in a mammal in need thereof, comprising the step of administering to said mammal a pharmacologically effective amount of the compound as claimed in claim 1.

9. A method of treating hypertension in a mammal in need thereof, comprising the step of administering to said mammal a pharmacologically effective amount of the compound as claimed in claim 1.

10. A method of inducing diuresis in a mammal in need thereof, comprising the step of administering to said mammal a pharmacologically effective amount of the compound as claimed in claim 1.

11. A method of inhibiting platelet agglutination in a mammal in need thereof, comprising the step of administering to said mammal a pharmacologically effective mount of the compound as claimed in claim 1.

* * * * *